Dec. 24, 1968 E. S. BOERNER Plant Pat. 2,851
ROSE PLANT
Filed March 16, 1967
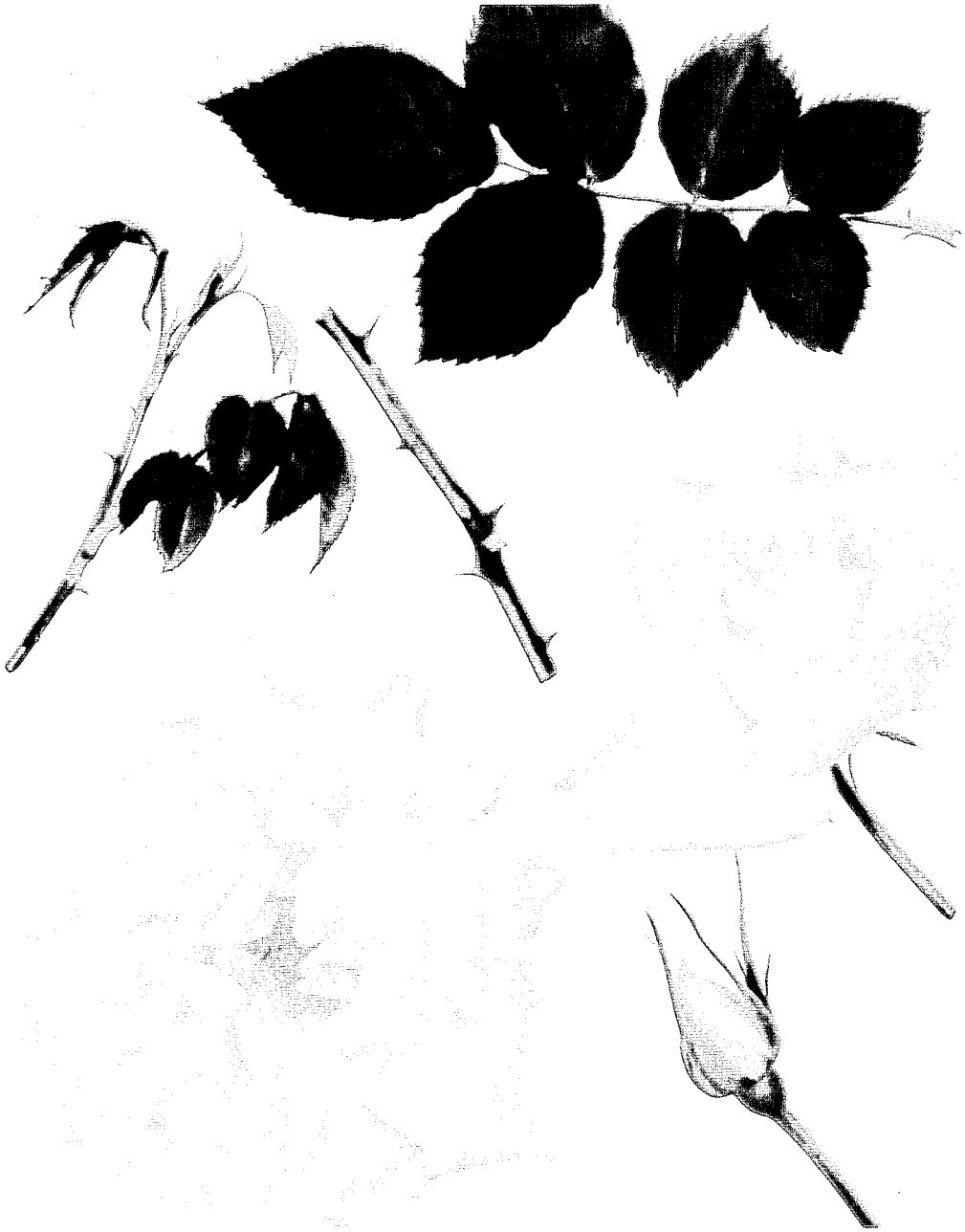
Inventor.
E. S. Boerner, Deceased
By: Lincoln Rochester Trust Company
By: Edward L. Jenner, Asst. Trust Officer
and Roger L. Boerner
Executors
By: Robb & Robb
Attorneys.

United States Patent Office

Plant Pat. 2,851
Patented Dec. 24, 1968

2,851
ROSE PLANT

Eugene S. Boerner, deceased, late of Benton, N.Y., by Lincoln Rochester Trust Co., Rochester, N.Y., and Roger L. Boerner, Milwaukee, Wis., executors, assignors to Jackson & Perkins Company, Newark, N.Y., a corporation of New York Filed Mar. 16, 1967, Ser. No. 624,967
1 Claim. (Cl. Plt.—26)

The present invention relates to a new and distinct variety of rose plant of the floribunda class, which was originated by the late Eugene S. Boerner, deceased, by crossing an unnamed and unpatented seedling of the hybrid tea rose variety known as "Summertime" (Plant Patent No. 1,541) with an unnamed and unpatented seedling of the fluoribunda rose variety known as "Spartan" (Plant Patent No. 1,357).

The primary objective of this breeding was to produce a larger flowered floribunda rose variety having long keeping cut flower qualities. This objective was fully achieved, along with other desirable improvements, as evidenced by the following unique combination of characteristics which are outstanding in the new variety and which distinguish it from its parents, as well as from all other varieties:

(1) A vigorous habit of growth;
(2) Strong flower stems suitable for cut flowers;
(3) A large flower size;
(4) A distinctive and attractive general color tonality of the flowers corresponding to La France Pink, lightly overcast with Eosine Pink, which is an improvement over the flower color of the rose "Summertime"; and
(5) Long keeping cut flower qualities.

Asexual reproduction of the new variety by budding, as performed at Newark, N.Y., and also at Pleasanton, Calif., shows that the aforementioned characteristics and distinctions come true to form and are established and transmitted through succeeding propagations.

The accompanying drawing shows typical specimens of the vegetative growth and flowers of the new variety in different stages of development and as depicted in color as nearly true as it is reasonably possible to make the same in a color illustration of this character.

The following is a detailed description of the new rose variety, with color terminology in accordance with Ridgway's Color Standards and Nomenclature:

Parentage: Seedling.
*Seed parent.*—An unnamed seedling of "Summertime."
*Pollen parent.*—An unnamed seedling of "Spartan."
Classification:
*Botanic.*—Floribunda.
*Commercial.*—Floribunda.

*Flower*

(Observations made from specimens grown in a greenhouse at Newark, N.Y., in the early morning during the first of the month of September.)

Blooming habit: Recurrent—continuous.
Bud:
*Size.*—Medium.
*Form.*—Ovoid; pointed; is not affected by wet or hot weather.
*Color.*—When sepals first divide—Scarlet-Red, Plate 1. When petals begin to unfurl—Scarlet-Red, Plate 1, lightly overcast with Peach Red, Plate 1, with the lower half of the petals overcast with Pale Chalcedony Yellow, Plate 17. When half-blown: inside of petals—Eosine Pink, Plate 1, overcast lightly with Thulite Pink, Plate 26; reverse of petals—Rose Pink, Plate 12, lightened with Cameo Pink, Plate 26, in the lower half of the petals.
*Sepals.*—Slightly branched; curl back when petals begin to unfurl. Color: inside—Light Grape Green, Plate 41; outside—Chromium Green, Plate 32.
*Calyx.*—Color—Light Cress Green, Plate 31. Shape—pear. Size—long. Aspect—smooth. Odor when rubbed—none.
*Peduncle.* — Length — medium. Aspect — rough. Strength—erect; slender. Color—Cress Green, Plate 31.
*Opening.*—Opens up well; is not affected by adverse weather conditions.

Bloom:
*Size.*—Large Average size when fully expanded—from 4 inches to 4½ inches.
*Borne.*—Both singly and several together.
*Stems.*—Medium length; strong.
*Form (when first open).*—High-centered. Permanence—retains its form to the end.
*Petalage.*—Double (full but open center). Number of petals under normal conditions—from 25 to 30.
*Color.*—Center of flower—Eosine Pink, Plate 1. Outer petals—Hermosa Pink, Plate 1, overcast lightly with Shrimp Pink, Plate 1. Base of petals (aiglet)—Naphthalene Yellow, Plate 16. Inside of petals—La France Pink, Plate 1, lightly overcast with Eosine Pink, Plate 1. Reverse of petals—Hermosa Pink, Plate 1, lightly overcast with Rose Pink, Plate 12. General tonality from a distance—La France Pink, Plate 1, very lightly overcast with Eosine Pink, Plate 1.
*Discoloration.*—General tonality at end of first day—Eosine Pink, Plate 1, lightly overcast with La France Pink, Plate 1. Second day—Eosine Pink, Plate 1, lightly overcast with La France Pink, Plate 1. Third day—Eosine Pink, Plate 1, overcast with La France Pink, Plate 1.

Petals:
*Texture.*—Thick.
*Appearance.*—Inside—satiny. Outside—shiny.
*Form.*—Oval; slightly notched.
*Arrangement.* — Imbricated (regularly arranged shingle-like).
*Petaloids in center.*—Few; large.
*Persistence.*—Drop off cleanly.
*Fragrance.*—Moderate. Nature—tea (average hybrid tea scent).
*Lasting quality.*—On the plant—very long. As cut flower—very long.

*Genital organs*

Stamens, anthers: Medium size; many; regularly arranged around styles. Color—Cinnamon, Plate 29.
Stamens, filaments (threads): Medium length. Color—Sea-Foam Yellow, Plate 31.
Pollen: Color—Light Pinkish-Cinnamon, Plate 29.
Styles: Bunched; uneven length; medium length; thin.
Stigmas: Color—Naples Yellow, Plate 16.
Ovaries: All enclosed in calyx.
Hips: None.
Seeds: None.

*Plant*

Form: Bush.
Growth: Vigorous; upright; branching.
Foliage: Compound of 5–7 leaflets.
*Size.*—Medium.
*Quantity.*—Normal.
*Color.*—New foliage: upper side—Dark Greenish Olive, Plate 30; under side—Madder Brown, Plate 13. Old foliage: upper side—Varley's Green, Plate 18; under side—Jade Green, Plate 31, with outer edge leaf lightly overcast with Acajou Red, Plate 13.

*Shape.*—Oval pointed.

*Texture.* — Upper side—leathery. Under side—smooth.

*Ribs and veins.*—Ordinary.

*Edge.*—Serrated (saw toothed).

*Serration.*—Both double and single; small.

*Leaf stem.*—Color—Light Hellebore Green, Plate 17. Under side—Prickly.

*Stipules.*—Medium length; smooth.

Wood:

*New wood.*—Color—Serpentine Green, Plate 16. Bark—smooth.

*Old wood.*—Color—Cress Green, Plate 31. Bark—smooth.

Thorns:

*Thorns.*—Quantity: on main stalks from base—few; on laterals from stalk—ordinary. Form—narrow base; medium length; some hooked downward and some hooked upward. Color (when young)—Nopal Red, Plate 1. Position—irregular.

*Prickles.*—Quantity: on main stalks—none; on laterals—none.

*Short needles.*—Quantity: on main stalks—none; on laterals—none.

What is claimed is:

1. A new and distinct variety of rose plant of the floribunda class, substantially as herein shown and described, characterized particularly as to novelty by the unique combination of a vigorous habit of growth, strong flower stems suitable for cut flowers, a large flower size, a distinctive and attractive general color tonality of the flowers corresponding to La France Pink, lightly overcast with Eosine Pink, which is an improvement over the flower color of the rose "Summertime," and long keeping cut flower qualities.

No references cited.

ROBERT E. BAGWILL, *Primary Examiner.*